United States Patent [19]

Cannon

[11] 4,235,757
[45] Nov. 25, 1980

[54] ETHYLENE EPOXIDATION CATALYST
[75] Inventor: James C. Cannon, Corpus Christi, Tex.
[73] Assignee: PPG Industries, Inc., Pittsburgh, Pa.
[21] Appl. No.: 79,298
[22] Filed: Sep. 27, 1979
[51] Int. Cl.³ .................... B01J 23/50; B01J 21/04; B01J 23/04; C07D 301/04
[52] U.S. Cl. .................... 252/476; 252/473; 260/348.34
[58] Field of Search .................... 252/476, 473, 430; 260/348.34, 584 R

[56] References Cited

U.S. PATENT DOCUMENTS

| | | | |
|---|---|---|---|
| 2,901,461 | 8/1959 | Auerbach et al. | 260/584 R |
| 3,962,136 | 6/1976 | Nielson et al. | 252/454 |
| 4,097,414 | 6/1978 | Cavitt | 252/476 |
| 4,126,582 | 11/1978 | Diem et al. | 252/476 |

FOREIGN PATENT DOCUMENTS 2002252  2/1979  United Kingdom .................... 252/476

*Primary Examiner*—P. E. Konopka
*Attorney, Agent, or Firm*—Edward J. Whitfield

[57] ABSTRACT

A silver containing ethylene epoxidation catalyst prepared by impregnating a support with a solution comprising a reducible silver compound and reducing the silver compound to metallic silver in the presence of a diaminoalkyl-alkanol, preferably, 2-(2-aminoethylamino)ethanol.

3 Claims, No Drawings

ETHYLENE EPOXIDATION CATALYST

BACKGROUND OF THE INVENTION

Ethylene oxide is typically prepared by catalytic oxidation of ethylene with oxygen. Metallic silver carried on an inert support material is typically employed as catalyst, the catalyst typically containing promoting amounts of other additives, for example, alkali metals or alkaline earth metals.

Such catalysts are typically prepared by impregnating the support material with a solution of silver compound followed by heating in the presence of a reducing agent to convert the silver compound to metallic silver. The reducing agent is usually a constituent of the impregnating solution and is deposited on the support material along with the catalytic actives, the reducing agent being volatized in the subsequent heating step.

The reducing agents are typically nitrogen containing organic compounds such as, for example, alkanol amines and alkylene diamines. According to U.S. Pat. No. 3,962,136 a combination of ethylene diamine with ethanolamine is most preferred as a reducing agent. However, ethylene diamine can coordinate with silver in either a monodentate or bidentate mode and monoethanolamine can compete with ethylene diamine for coordination sites, with the result that a mixture of complexes having different component ratios can be formed, which could result in variations in the effectiveness of reduction of silver complex to silver metal with the consequence that catalytic activity and selectivity could vary from catalyst to catalyst.

Since in the production of ethylene oxide by catalytic oxidation of ethylene with oxygen the overall economics of the process are very sensitive to raw materials cost catalytic selectivity is extremely important and even relatively small variations in selectivity are crucial from the standpoint of operations economics.

DESCRIPTION OF THE INVENTION

In accordance with this invention it has been found that in the production of silver catalyst, expecially useful in catalyzing the reaction between ethylene and oxygen, a support material is impregnated with a solution comprising a silver compound. The silver compound is reduced to silver metal in the presence of a reducing agent represented by the formula:

$$NH_2—R—NH—R_1—OH$$

Wherein R and $R_1$ are the same or different and represent alkylidene radicals having 2 to 4 carbon atoms. Of compounds represented by the above formula 2-(2-aminoethylamino)ethanol has been found to be eminently suited for use as the reducing agent, although other compounds within the scope of the general formula are also believed to be suitable for use in accordance with the invention.

In a preferred embodiment of the invention, a support material is impregnated with a solution comprising silver compound and reducing agent and heated to evaporate volatiles, reduce the silver complex to metallic silver and activate the catalyst. More particularly the impregnating solution may be prepared by combining silver oxide, oxalic acid, and 2-(2-aminoethylamino)ethanol in water to yield a solution containing silver oxalate 2(2-aminoethylamino)ethanol complex. The impregnating solution may also contain other additives known to promote ethylene oxide production. Selectivity of silver catalysts may be enhanced by inclusion of, for example, salts and oxides of alkali and alkaline earth metals, more particularly salts and oxides of sodium, potassium, rubidium, cesium, strontium, calcium, barium and the like which promoters as well as others are described, for example, in U.S. Pat. No. 4,007,135.

Typically, the impregnating solution contains sufficient silver compound so that the finished catalyst contains from about 2 to about 30 weight percent silver, and sufficient of the promoting compounds so that the finished catalyst contains up to about 1000 parts per million of the particular promotor exclusive of any of the promoting material that may be intrinsically present in the support material. Sufficient 2-(2-aminoethylamino)ethanol is used in sufficient amount so as to complex substantially all of the silver in the impregnating solution.

As to choice of support material, the same may be any porous, inorganic material known to the ethylene epoxidation art and which material may be in granular or monolithic form. Some examples of suitable support materials are glass, alumina, zirconia, and the like.

The support material is contacted with the impregnating solution by immersing the support material in the solution, and subjecting the immersed material to evacuation to remove air entrapped in the pores, the immersion and evacuation typically being conducted at ambient temperature. The time of immersion depends on the nature of the support material and may vary from several minutes to several hours.

The impregnated support material is drained of excess liquid and heated to evaporate volatiles, reduce the silver complex to silver metal and activate the catalyst. The heating temperature and heating time may vary over a wide range; typically temperatures of 150° C. to 500° C. are employed with the heating time typically ranging from one to several hours.

It will be realized that all of the steps described herein regarding manufacture of ethylene epoxidation catalyst are well-known to the art, the invention residing in the use of a particularly defined class of reducing agents which embody both amino and hydroxyl functionalities in a single compound which permits the formation of only one type of ligand structure between silver and the reducing compound, so that only one class of complex having a constant N to OH ratio may be formed.

The invention is further illustrated by the following examples:

EXAMPLE 1

An impregnating solution was prepared by dissolving in 51 milliliters of water 45 grams of 2-(2-aminoethylamino)ethanol, 30 grams of oxalic acid and 50 grams of silver oxide. To this solution was added 18 milliliters of calcium acetate solution (115.4 grams $Ca(CH_3COOH)_2.H_2O$ per liter of water) and 1.8 milliliters of potassium nitrate solution (13.5 grams $KNO_3$ per liter of water). The solution was poured over 160 grams of Norton Co. SA-5552 alumina support rings. The support was impregnated by tumbling under vacuum for 15 minutes using a rotary film evaporator connected to a vacuum pump. Excess liquid was drained off and the impregnated support was heated in an oven for 3½ hours at 300° C.

The catalyst was tested in a laboratory scale continuous stirred tank catalyst reactor, also called a gradientless reactor, containing 75 grams of catalyst. The catalyst was contacted with a feed gas containing 5 percent carbon dioxide, 18 percent ethylene, 7.6 percent oxygen, 0.5 parts per million ethylene dichloride and the balance nitrogen at 300 psig and a flow rate of 9 standard liters per minute (space velocity=7200 $hr^{-1}$ $kg^{-1}$). After steady state operation was achieved, the catalyst was found to have an ethylene oxide selectivity of 73.1±.2.1 percent with an ethylene oxide yield of 1.04 ±0.07 percent over the temperature range of 440°–455° F.

EXAMPLE 2 (COMPARISON)

A catalyst was prepared in like manner as the catalyst of Example 1 except that 26.3 grams of ethanolamine, 26.4 grams of ethylene diamine and 40 milliliters of water were used in place of the 45 grams of 2-(2-aminoethylamino) ethanol and 51 milliliters of water to yield an equivalents volume of amine and water to that used in Example 1 and to duplicate the functional groups, i.e., 0.43 moles each of ethylene diamine and monoethanol amine were used in this Example 2, wherein 0.43 mole of 2-(2-aminoethylamino)ethanol was used in Example 1.

Seventy-five grams of catalyst prepared in accordance with this Example 2 were tested under identical conditions as the catalyst prepared in Example 1 and the catalyst was found to have an ethylene oxide selectivity of 67.1±0.7 percent with an ethylene oxide yield of 0.99±0.03 percent.

I claim:

1. A silver containing catalyst suitable for use in preparing ethylene oxide by the oxidation of ethylene with oxygen said catalyst prepared by impregnating a support material with a solution of catalytic actives followed by heating the support material in the presence of a reducing agent to deposit metallic silver on the support material, the improvement wherein the reducing agent is a compound represented by the formula:

$$NH_2-R-NH-R_1-OH$$

wherein R and $R_1$ are the same or different and selected from alkylidene radicals containing from 2 to 4 carbon atoms.

2. The improvement of claim 1 wherein the reducing agent is 2-(2-aminoethylamino)ethanol.

3. The improvement of claim 1 wherein the reducing agent is a constituent of the solution used to impregnate the support material.

* * * * *